(12) United States Patent
Qin et al.

(10) Patent No.: US 9,757,728 B2
(45) Date of Patent: Sep. 12, 2017

(54) MICROFLUIDIC ALIQUOTING FOR SINGLE-CELL ISOLATION

(71) Applicants: Lidong Qin, Houston, TX (US); Kai Zhang, Manvel, TX (US)

(72) Inventors: Lidong Qin, Houston, TX (US); Kai Zhang, Manvel, TX (US)

( * ) Notice: Subject to any disclaimer, the term of this patent is extended or adjusted under 35 U.S.C. 154(b) by 0 days.

(21) Appl. No.: 15/006,634

(22) Filed: Jan. 26, 2016

(65) Prior Publication Data
US 2017/0209863 A1   Jul. 27, 2017

(51) Int. Cl.
| | | |
|---|---|---|
| B01L 3/00 | (2006.01) | |
| F15D 1/00 | (2006.01) | |
| G01N 21/03 | (2006.01) | |
| C12Q 1/04 | (2006.01) | |
| C12Q 1/00 | (2006.01) | |
| G01N 30/00 | (2006.01) | |
| G01N 1/10 | (2006.01) | |

(52) U.S. Cl.
CPC ....... B01L 3/502761 (2013.01); B01L 3/5027 (2013.01); C12Q 1/04 (2013.01); *B01L 3/5023* (2013.01); *B01L 2200/0652* (2013.01); *B01L 2200/10* (2013.01); *B01L 2300/0803* (2013.01); *B01L 2300/0806* (2013.01); *B01L 2300/0864* (2013.01); *B01L 2300/0893* (2013.01); *B01L 2300/123* (2013.01); *B01L 2400/0487* (2013.01)

(58) Field of Classification Search
CPC ..... B01L 2300/0803; B01L 2300/0806; B01L 2200/10; B01L 3/5027; B01L 3/5023; B01L 2300/0864; B01L 2400/0409; B01L 2300/087; B01L 2300/0877; B01L 2300/0867; B01L 3/502715; C12M 23/16; G01N 2035/0439
See application file for complete search history.

(56) References Cited

U.S. PATENT DOCUMENTS

| | | | | |
|---|---|---|---|---|
| 6,632,656 | B1 * | 10/2003 | Thomas | B01L 3/5027 435/288.5 |
| 8,329,437 | B1 * | 12/2012 | Ayliffe | G01N 15/1056 422/68.1 |
| 9,164,111 | B2 * | 10/2015 | Symonds | G01N 21/253 |
| 2006/0133958 | A1 * | 6/2006 | Hsieh | B01L 3/502723 422/72 |
| 2009/0227041 | A1 * | 9/2009 | Wang | G01N 35/00069 436/180 |

(Continued)

*Primary Examiner* — Jennifer Wecker
(74) *Attorney, Agent, or Firm* — Michael D. Eisenberg

(57) ABSTRACT

According to the invention, generally, a microfluidic aliquoting (MA) chip, adapted to fit in a Petri dish, has a center well (inlet) connected by a plurality of microchannels to a plurality of side wells (outlets). A relatively large (such as 120 μL) cell suspension having several cells may be injected into the inlet of the MA chip, and single cells may be substantially simultaneously and uniformly distributed, via positive pressure-driving flow, to the several (such as 120) side wells having single cells in less than 1 minute. The MA Chip has a high efficiency in cell recovery. Due to rapid isolation and easy identification of single cells, high cell viability, high enrichment factor, and convenient transfer of submicroliter single-cell suspension, MA Chips are well compatible with CTC isolation from blood, single-cell cloning, PCR, and sequencing.

26 Claims, 3 Drawing Sheets

(56) References Cited

U.S. PATENT DOCUMENTS

| | | | |
|---|---|---|---|
| 2010/0212436 A1* | 8/2010 | Swenson | G01N 1/2208 73/863.22 |
| 2011/0038766 A1* | 2/2011 | Kitamura | B01L 3/502723 422/502 |
| 2014/0004557 A1* | 1/2014 | Ma | C12M 21/06 435/29 |

* cited by examiner

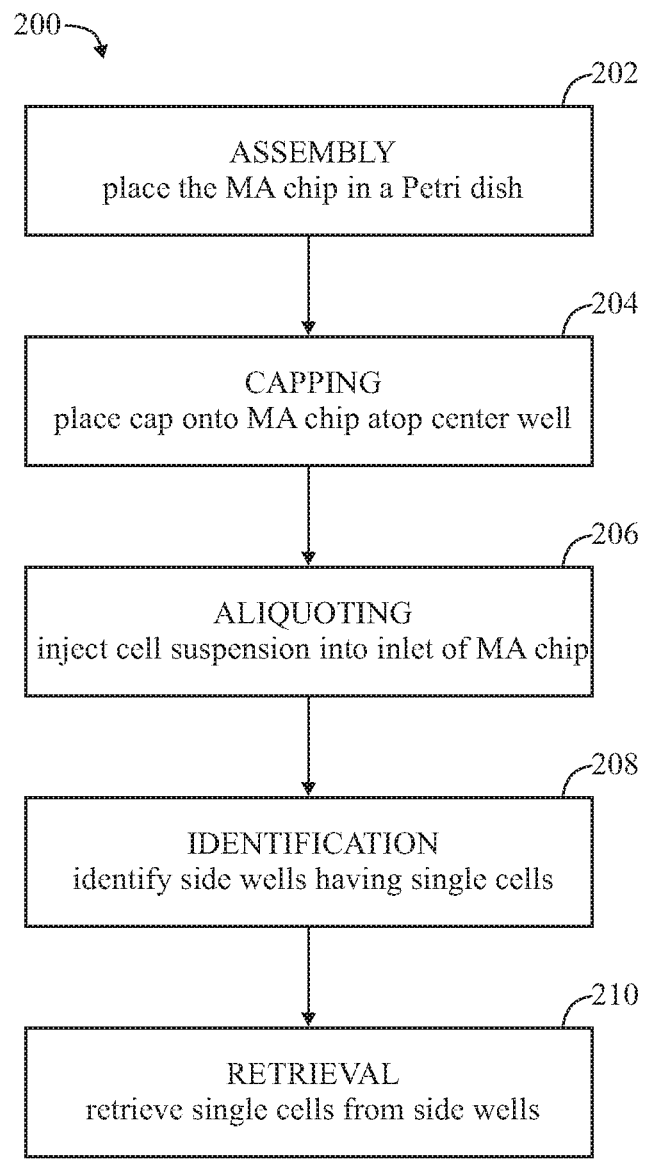

MICROFLUIDIC ALIQUOTING FOR SINGLE-CELL ISOLATION

TECHNICAL FIELD

The present invention, in some embodiments thereof, relates broadly to methods and apparatus for single-cell isolation (such as for processing or analysis) and, more particularly to techniques for isolating single cells using microfluidic technology.

BACKGROUND

Microfluidics is a multidisciplinary field intersecting engineering, physics, chemistry, biochemistry, nanotechnology, and biotechnology, with practical applications to the design of systems in which low volumes of fluids are processed to achieve multiplexing, automation, and high-throughput screening. Advances in microfluidics technology are revolutionizing molecular biology procedures for enzymatic analysis (e.g., glucose and lactate assays), DNA analysis (e.g., polymerase chain reaction and high-throughput sequencing), and proteomics. The basic idea of microfluidic biochips is to integrate assay operations such as detection, as well as sample pre-treatment and sample preparation on one chip.

There is increased evidence that phenotypic and genotypic heterogeneity in cell populations widely exists. The key information from individual rare cells may be masked by bulk cell analysis. Single-cell analysis, especially sequencing of DNA and RNA, has therefore become significantly important for clonal mutation, tumor evolution, embryonic development, and immunological intervention.

The initial and key step for such downstream single-cell genetic analysis is to effectively isolate live single cells of interest from heterogeneous cell populations into submicroliter medium volume, followed by PCR (polymerase chain reaction) analysis. (PCR is a technology in molecular biology used to amplify a single copy or a few copies of a piece of DNA across several orders of magnitude, generating thousands to millions of copies of a particular DNA sequence.)

Besides laser capture microdissection primarily used to isolate single cells from formalin-fixed paraffin-embedded tissue, there are currently four main approaches for single-cell isolation from cell suspensions.

As the most frequently used method, serial dilution has been widely applied for colony formation but not suited for PCR analysis where single cells should be isolated into submicroliter suspensions for better amplification reaction. Even so, these colonies are still required for further analysis to judge if they originate from single cells which are very difficult to be accurately counted after seeding into 96-well plates.

Micromanipulation is mainly developed to isolate single cells for genome/transcriptome sequencing; however time consuming process and low throughput feature make it difficult to meet the increased requirement of rapid preparation of dozens and even hundreds of single cells10. Moreover, it seems to be very much relied on personal skills when using a researcher's mouth power to suck single cells.

Flow cytometry is a well-established method particularly suitable for high-throughput sorting of specific cells based on a preset fluorescence gating strategy, but maintenance of high single-cell viability is challenging and it doesn't work when only a limited number of cells, such as precious clinical samples, are available.

Due to comparable size dimension of microchannel and cell, recently developed microfluidic technology provides an important way for single cell manipulation; however potential disadvantages, such as requiring additional skills for microfluid manipulation, poor compatibility with existing experimental platform, and unable/difficult to selectively retrieve the isolated single cells from microchips for further analysis, greatly limit their application in common laboratories.

U.S. Pat. No. 6,632,656 (2003-10-14; Thomas et al.), incorporated by reference herein, discloses apparatus and methods for performing cell growth and cell based assays in a liquid medium. The apparatus comprises a base plate supporting a plurality of micro-channel elements, each micro-channel element comprising a cell growth chamber, an inlet channel for supplying liquid sample thereto and an outlet channel for removal of liquid sample therefrom, a cover plate positioned over the base plate to define the chambers and connecting channels, the cover plate being supplied with holes to provide access to the channels. Means are incorporated in the cell growth chambers, for cell attachment and cell growth. More particularly, as shown and described therein:

Referring to FIG. 1b, the apparatus comprises a rotatable disc (18) microfabricated to provide a sample introduction port located towards the centre of the disc and connected to an annular sample reservoir (9) which in turn is connected to a plurality of radially dispersed micro-channel assay elements (6) each of said micro-channel elements comprising a cell growth chamber, a sample inlet channel and an outlet channel for removal of liquid therefrom and a cover plate positioned onto said disc so as to define closed chambers and connecting channels. Each micro-channel element is connected at one end to the central sample reservoir (9) and at the opposing end to a common waste channel (10).

Each of the radially-dispersed micro-channel elements (6) of the microfabricated apparatus (shown in FIG. 1a) comprises a sample inlet channel (1) connected at its left hand-end end to the reservoir (9), a cell growth chamber (2) for performing cell growth and connected through a channel (4) to an assay chamber (3) and an outlet channel (5) connected at its right-hand end to the waste channel (10).

Suitably the disc (18) is of a one- or two-piece moulded construction and is formed of an optionally transparent plastic or polymeric material by means of separate moldings which are assembled together to provide a closed structure with openings at defined positions to allow loading of the device with liquids and removal of waste liquids. In the simplest form, the device is produced as two complementary parts, one or each carrying moulded structures which, when affixed together, form a series of interconnected micro-channel elements within the body of a solid disc. Alternatively the micro-channel elements may be formed by micro-machining methods in which the micro-channels and chambers forming the micro-channel elements are micro-machined into the surface of a disc, and a cover plate, for example a plastic film, is adhered to the surface so as to enclose the channels and chambers.

The scale of the device will to a certain extent be dictated by its use, that is the device will be of a size which is compatible with use with eukaryotic cells. This will impose a lower limit on any channel designed to allow movement of cells and will determine the size of cell containment or growth areas according to the number of cells present in each assay. An average mammalian cell growing as an adherent culture has an area of ~300 $\mu m^2$; non-adherent cells and non-attached adherent cells have a spherical diameter of ~10 $\mu m$. Consequently channels for movement of cells within the device are likely to have dimensions of the order of 20-30 $\mu m$ or greater. Sizes of cell holding areas will depend on the number of cells required to carry out an assay (the number being determined both by sensitivity and statistical requirements). It is envisaged that a typical assay would require a minimum of 500-1000 cells which for adherent cells would require structures of 150,000-300,000 $\mu m^2$, i.e. circular 'wells' of ~400-600 $\mu m$ diameter.

The configuration of the micro-channels . . . is preferably chosen to allow simultaneous seeding of the cell growth chamber by application of a suspension of cells in a fluid medium to the sample reservoir by means of the sample inlet port, followed by rotation of the disc (18) by suitable means at a speed sufficient to cause movement of the cell suspension outward towards the periphery of the disc by centrifugal force. The movement of liquid distributes the cell suspension along each of the inlet micro-channels (1, 8) towards the cell growth chambers (2, 7). The rotation speed of the disc is chosen provide sufficient centrifugal force to allow liquid to flow to fill the cell growth chamber (2, 7), but with insufficient force for liquid to enter the restricted channel (4, 16) of smaller diameter on the opposing side of the cell growth chamber.

SUMMARY

It is an object of the invention to provide a technique (method and apparatus) for simple, rapid, and versatile single-cell isolation.

Aliquoting generally refers to taking a representative sample from a larger amount of a substance, typically a liquid. In this case, aliquoting refers to isolating a single cell from a suspension having a large number of cells. This process is done in a liquid environment, using microfluidic technology, and is thus referred to as "microfluidic aliquoting".

According to the invention, generally, a microfluidic aliquoting (MA) chip (or substrate, which may be referred to as "MA chip", "MA-chip", or variants thereof), which may be in the form of a disc and which may be adapted to fit in a Petri dish, has a center well (inlet) connected by a plurality of microchannels (channels) to a plurality of side (or outer) wells (outlets). In operation, a cell suspension having few (such as approximately 2-120) cells may be injected into the inlet of the MA chip (pushed into the center well by pipette with positive pressure), and single cells may be displaced (moved, transported) through the microchannels to some of the side (outer) wells via positive pressure-driving flow.

According to some embodiments (examples) of the invention, a Microfluidic aliquot (MA) chip for performing single-cell isolation may comprise: a chip in the form of a disc having a radius, a center, a top surface, a bottom surface, an outer edge and a thickness; a single center well (inlet) disposed substantially at the center of the chip, extending into and accessible from the top surface of the chip; a plurality of side wells (outlets) disposed in an annular outer portion of the chip, extending into and accessible from the top surface of the chip; and a plurality of channels extending into the bottom surface of the chip and extending from the center well to the side wells in fluid communication with the center well and the side wells.

The chip may comprise a thin sheet of flexible or semi-rigid material selected from the group consisting of polydimethylsiloxane (PDMS), PMMA (poly(methyl methacrylate)), PS (polystyrene), and PC (polycarbonate). The chip may have a thickness of approximately 1 mm, may be sized and shaped to fit within a Petri dish; and may have a radius of approximately 3 cm. The center well may extend completely through the chip; and the side wells may extend completely through the chip.

The center well may have a diameter of approximately 3 mm and a volume of approximately 4 $\mu l$. At least some of the side wells may have a diameter of approximately 1.5 mm and a volume of approximately 1 $\mu l$.

A first set of the plurality of side wells may be disposed at a first radius (r1) from the center of the chip and a second set of the plurality of side wells may be disposed at a second radius (r2) from the center of the chip. The second radius (r2) may be greater than the first radius (r1). The first and second sets of side wells may be interleaved such that the second set of side wells are disposed at circumferential positions between the first set of sixty side wells. The first and second sets of side wells may be distributed evenly around the annular outer portion of the chip. annular outer portion of the chip may extend from at least 70% of the radius of the chip to an outer edge of the chip.

The channels may extend radially from the center well to the side wells. The channels may extend only partially into the chip. The channels may have a width of approximately 30 $\mu m$. The channels may be sized and shaped to accommodate transport of single cells from the center well to the side wells.

The MA chip may further comprise: relatively small $\mu m$-scale markings disposed inboard of at least some of the side wells for uniquely identifying the side wells under microscopic observation; and relatively large mm-scale markings disposed outboard of at least some of the side wells for uniquely identifying the side wells under naked-eye observation.

The MA chip may further comprise a cap having a hole extending therethrough, adapted in use to be disposed atop the center well, for facilitating loading of a cell suspension into the center well. The cap may be cylindrical and may comprise a lip or shoulder extending from a bottom surface thereof to within the center well to temporarily secure the cap in place during loading of the cell suspension. The cap may be formed integrally with the chip.

According to some embodiments (examples) of the invention, a method of isolating single cells from a cell suspension having a few cells may comprise: injecting a cell suspension having a few cells into an inlet of a microfluidic aliquot (MA) chip having a single center well and a plurality side wells connected by a plurality microchannels to the center well; and displacing single cells via the microchannels to the side wells by positive-pressure driving flow.

The method may comprise identifying and isolating single or rare circulating tumor cells (CTCs) from blood, wherein the CTCs are captured in the side wells after single or multi-step MA Chip operations. The method may comprise identifying and isolating single cells and objects from a complicated matrix, including isolating single objects including bacterial, beads, particles, virus from a matrix, including isolating Tuberculosis, and to isolate single clones, including isolating yeast cells of a particular genotype/phenotype. The method may comprise identifying cells in the side wells and retrieving cells from the side wells containing only single cells.

According to some embodiments (examples) of the invention, a method of performing single-cell analysis may comprise: providing a microfluidic aliquot (MA) chip comprising: a chip in the form of a disc having a center and a surface; a single center well (inlet) disposed substantially at the center of the chip; a plurality of side wells (outlets) disposed in an annular outer portion of the chip; and a plurality of channels extending from the center well to the side wells. The method may further comprise: injecting a cell suspension into an inlet of a microfluidic aliquot (MA) chip having a single center well and a plurality side wells connected by a plurality microchannels to the center well; and displacing single cells via the microchannels to the side wells by positive-pressure driving flow. The method may further comprise adding cell-free media into the center well to generate positive hydrostatic pressure to cause single cells residual in the channels to flow into the side wells.

Microfluidic aliquoting, as described herein, may allow for convenient, rapid, identifiable, and damage-free single-cell isolation, independent of cell size, shape, and motility. The isolated single cells can either proliferate to form cloning within the side wells or can be easily retrieved from the side wells as submicroliter single-cell suspensions for subsequent PCR and sequence analysis. Due to high efficient enrichment ability, the method can also be applied to isolate single cancer cells from blood.

Splitting a limited liquid into multiple aliquots with equal volume by single/multi-channel pipette for parallel analysis is a universal experimental process in biological and chemical laboratories, for example serial dilution which has been widely used to isolate single cells from cell suspension via manual/automatic pipette. However, large aliquot volume and difficulty in accurately identifying single cells make it incompatible with single-cell genetic analysis and also very time consuming.

By comparison, microfluidic aliquoting, as disclosed herein, has significant advantages in reducing both aliquot volume and labor. Several (such as 120) submicroliter aliquots can be well prepared within 1 minute and single wells containing single cells can be rapidly and accurately identified (such as at a rate of 1 well per second) under a common inverted microscope.

Microfluidic aliquoting provides a simple and effective strategy to rapidly obtain multiple submicroliter aliquots with minimum sample loss (about 18 nL per well, which may be substantially equal to a single microchannel volume). It is a facile and experience-insensitive method without the requirement of complex instruments, additional training, and even background knowledge of microfluidics.

Besides the MA chip disclosed herein, some other equipment involved in the process, such as pipettes, Petri dish, and optical microscope are usually readily available in common laboratories. Liquid handling during the whole procedure containing introduction of original cell suspension and transfer of single-cell suspensions is achieved only by pipette, making it more accessible to a beginner.

Some features and advantages of using the MA chip for single-cell isolation may include:

Easy operation. Both single-cell suspension introduction and collection may be completed only by using commonly-used air displacement pipette without any requirement of pre-training.

Fast sample introduction. Dispensing single cell suspension into 120 (one hundred twenty) 1 µl volume side wells may only require less than 1 minute.

Easy identification of single cells. Single cells within 1.5 mm diameter side wells can be very easily identified under common optical microscope (one well per second).

Easy to track side wells. Each 1.5 mm diameter side well is marked simultaneously by small microscale-size numbers for microscope observation and large macroscale-size numbers for naked eye observation.

Compatible with single-cell PCR. Single cell can be isolated into approximately 1 µl volume liquid and transferred into vial by commonly used pipette for subsequent single-cell PCR and sequence.

High cell viability and compatible with cloning formation. The isolated single cells are healthy and can proliferate normally within side wells until to form cloning.

Selective single-cell isolation. Single cells can be selectively isolated based on size, suspended/adherent shape, and fluorescence, such as isolation of circulating tumor cells (CTCs) from blood.

High throughput operation. One MA chip provides 120 (one hundred twenty) side wells for single cell isolation and analysis.

High compatibility with different cell size and shape. Both single eukaryocyte cells and single prokaryotic cells with diameters from 1 µm to 30 µm can be effectively isolated into 1 µl volume side wells.

Low cost. In mass production, the cost of each MA chip may be less than 1 dollar.

Sterilization. The MA chip can be sterilized by standard ways including autoclave, alcohol soak, and UV exposure.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 2 is a flow diagram of a method of microfluidic aliquoting.

The figures are not intended to be exhaustive or to limit the invention to the precise form disclosed. It should be understood that the invention can be practiced with modification and alteration, and that the invention be limited only by the claims and the equivalents thereof.

DESCRIPTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs.

All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Any dimensions set forth herein should be regarded as exemplary and approximate, unless otherwise indicated in the description, and may be interpreted to indicate the relative scale of various elements which may be described.

According to the invention, generally, a relatively large (such as 120 μL) cell suspension having several cells may be substantially simultaneously and uniformly distributed (divided) into several (such as 120) aliquots having single cells in less than 1 minute. Random and reliable single-cell isolation may be achieved using a microfluidic aliquot chip (MA Chip) having a single center well in fluid communication, via several individual microchannels, with several individual side wells. The MA chip can be used to effectively isolate single cells in the side wells, by positive pressure-driving flow, from a few (such as approximately 2-120) cells in the center well. The MA Chip has a high efficiency in cell recovery. Due to rapid isolation and easy identification of single cells, high cell viability, and convenient transfer of submicroliter single-cell suspension, MA Chips are well compatible with single-cell cloning, PCR, and sequencing.

An Exemplary MA Chip

Figure 1:
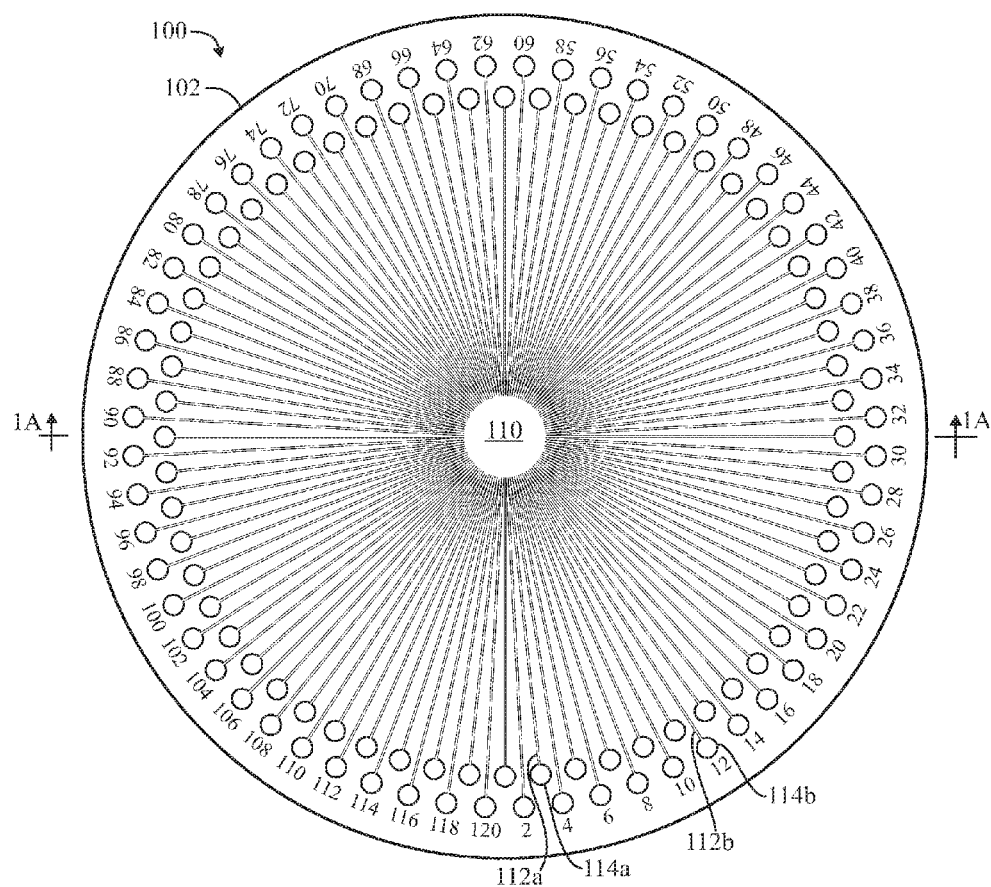
FIG. 1 is a diagram, in plan view, of an exemplary Microfluidic Aliquoting (MA) chip.
Figure 1A:
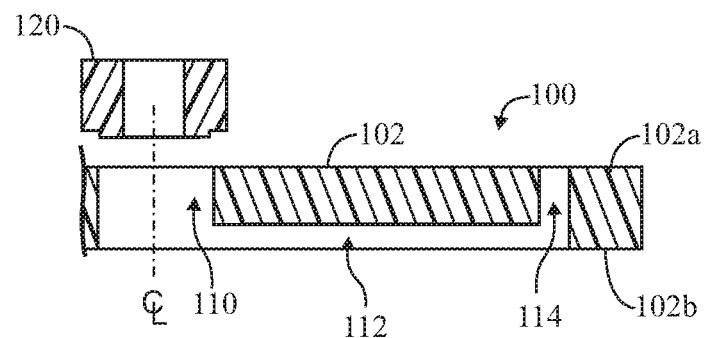
FIG. 1A is a diagram, in cross-sectional view, of a portion of the MA chip of FIG. 1, taken on a line 1A-1A through FIG. 1. (The view of FIG. 1A extends from the right edge of the MA chip to slightly to the left of the center well.)
Figure 1B:
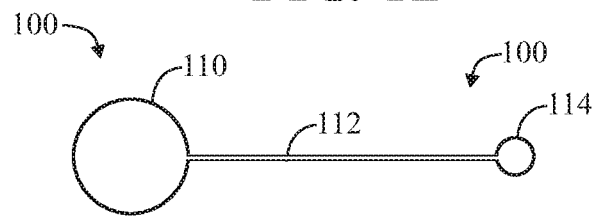
FIG. 1B is a diagram, in plan view, magnified, of a portion of the MA chip of FIG. 1.
Figure 1C:
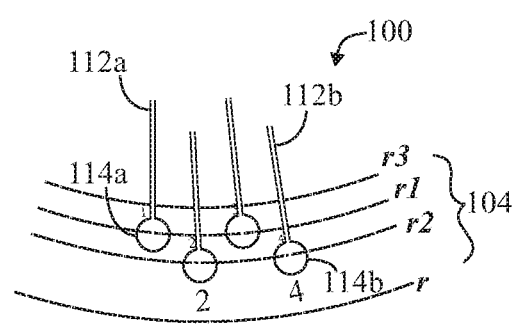
FIG. 1C is a diagram, in plan view, magnified, of a portion of the MA chip of FIG. 1.

FIG. 1 shows an overall view of an exemplary Microfluidic Aliquoting (MA) chip 100, which may be referred to herein as the "MA chip". FIG. 1A shows a portion of the MA chip of FIG. 1. FIG. 1B shows a portion (magnified) of the MA chip of FIG. 1. FIG. 1C shows a portion (magnified) of the MA chip of FIG. 1.

The MA chip may comprise a thin sheet 102 of a flexible or semi-rigid material such as polydimethylsiloxane (PDMS), having a thickness of approximately 1 mm. The MA chip may have the overall form of a disc, having a geometric center (CL) and a diameter of approximately 6 cm (a radius of approximately 3 cm). The MA chip may have an overall weight of approximately 1.7 g. The MA chip may be sized and shaped to fit in a Petri dish having a diameter of approximately 8.5 cm. The sheet forming the MA chip may have a top surface 102a and a bottom surface 102b, corresponding to the top and bottom surfaces of the overall MA chip, respectively.

The MA chip may be other than in the form of a disc, such as a polygon. In the main, hereinafter, an MA chip which is a disc will be described.

In the main, hereinafter, various features (center well, side wells, channels) extending into the top and bottom surfaces of the MA chip, including completely through the MA chip will be described.

The MA chip has a single (one) center well 110, connected by a plurality of channels 112a, 112b (which may collectively be referred to as "112") extending radially from the center well to a like plurality of side wells 114a, 114b (which may collectively be referred to as "114"). The channels 112 are in fluid communication with the center well 110 and the side wells 114.

The center well 110 may serve as an inlet, and may be in the form of a round hole extending at least partially, such as approximately 500 μm, into the top surface of the MA chip. As best viewed in FIG. 1A, the center well may extend completely through the MA chip. The center well may have a diameter of approximately 3 mm. The center well may have a volume of 4 μl. The center well may be disposed at the geometric center of the MA chip. The center well is accessible to a user from the top surface of the MA chip, for loading a cell suspension into the MA chip.

The side (or outer) wells 114 may serve as outlets, and may be in the form of round holes extending at least partially, such as approximately 500 μm, into the top surface of the MA chip. As best viewed in FIG. 1A, the side wells may extend completely through the MA chip. The side wells may have a diameter of approximately 1.5 mm. The side wells may each have a volume of 1 μl. The side wells may be distributed around an outer circumferential (or annular) portion (which may be referred to herein as the "circumference") of the MA chip. The side wells are accessible to a user from the top surface of the MA chip, for retrieving isolated cells from the MA chip.

There may be, for example, 120 (one hundred twenty) side wells 114. The several side wells may be arranged into a first set 114a of side wells disposed at a first radius (r1) from the center of the MA chip, and a second set 114b of side wells disposed at a second radius (r2) from the center of the MA chip. For example, the first set of side wells may comprise 60 (sixty) side wells arranged (disposed, distributed) evenly (every 6 degrees) around the circumference of the MA chip at a radius (r1) of 25 mm from the geometric center of the MA chip. And, the second set of side wells may comprise 60 (sixty) side wells arranged (disposed, distributed) evenly (every 6 degrees) around the circumference of the MA chip at a radius (r2) of 28 mm from the geometric center of the MA chip. The first and second sets of side wells may be interleaved (staggered), such that the second set of sixty side wells are disposed at circumferential positions between the first set of sixty side wells, in which case there would be one hundred twenty side wells disposed evenly, every 3 (three) degrees around the outer circumferential portion (or simply, "circumference") of the MA chip. Other numbers (more or less) and arrangements of side wells are possible. In FIG. 1, only some of the side wells 114a and 114b are labeled (with reference numerals), for illustrative clarity. FIGS. 1A and 1B refer generally to a side well 114 which may be either of one of the first set of side wells 114a or one of the second set of side wells 114b. FIG. 1C shows only four (of the 120) of the side wells 114a and 114b, and some are labeled with reference numerals.

The MA chip 100 may be in the form of a disc having a center, and a radius of 3 cm. The center well may be disposed at the center of the disc. The side wells may be disposed at radii of 25 mm or 28 mm from the center of the disc in what has been referred to as an "outer circumferential portion" (or "annular outer portion") of the disc. This annular outer portion of the disc (whereat the side wells are located) may be defined as that portion of the disc which extends from a radius r3 which is approximately at least 50% (such as at least 60% or at least 70% or at least 75% or at least 80%, or at least 90%, up to approximately nearly 100% of the overall radius r of the disc to the outer edge (100% radius, "r") of the disc. See element 104 in FIG. 1C.

The outer circumferential portion (or region) of the MA chip may be an annulus. An annulus is a ring-shaped region bounded by two concentric circles. FIG. 1C shows a portion of the MA chip, which may be disc-shaped, having a radius r. (The center of the MA chip is out of the view.) The first set of side wells 114a may be disposed at a radius r1 from the center of the MA chip. The second set of side wells 114b may be disposed at a radius r2 from the center of the MA chip, wherein r2 is greater than r1(r2>r1). The outer circumferential portion of the MA chip may extend from a radius r3 from the center of the MA chip to the outer edge of the MA chip which is at a radius r from the center of the MA chip, and the radius r3 may be less than the radius r1 (r3<r1).

The channels 112, which may be referred to herein as "microchannels", may be elongated, having a length and a width, and may extend at least partially, such as 30 μm (which is only partially, if the chip is 1 mm thick), into the bottom surface of the MA chip. This may best be viewed in FIG. 1A. Although preferably extending only partially through the MA chip, the microchannels may extend completely through the MA chip. The microchannels may have a width of 30 μm. Dimensions of the microchannels between 20 μm and 100 μm, in both depth and width, are acceptable.

The microchannels 112 may extend radially from the center well to the side wells, such as from the outer edge of the center well to the inner edges of the side wells. There may be one microchannel for each side well. Thus, for example, there may be 120 (one hundred twenty) microchannels extending from the single (one) center well to the 120 (one hundred twenty) side wells. The microchannels generally provide for fluid communication, and transport (movement) of cells, between the center well (inlet) and the side wells (outlets). The microchannels may be regarded as channels, canals, conduits, or connectors for connecting the inlet to the outlets. One end of each microchannel may connect to (fluidly communicate with) the center well, while the other end of each microchannel may connect to (fluidly communicate with) a given one of the plurality of side wells. Alternatively, the microchannels may extend other than radially from the outer well to the side wells (such as in the manner of spokes extending from the hub to the rim of a spoked wheel).

Since the side wells may be arranged at different radii (r1, r2) from the center of the MA chip, the microchannels may be arranged as a first set 112a of 60 (sixty) microchannels extending to the first set 114a of side wells, and a second set of 60 (sixty) microchannels extending to the second set 114 of side wells. The first set of microchannels may have a length of approximately 23 mm. The second set of microchannels may have a length of approximately 25 mm. Since the side wells are staggered (r1, r2, r1, r2), the longer, second set of microchannels 112b may need to pass between two adjacent ones of the first set of side wells 114a. (The shorter, first set of microchannels 112a extend to the first set of side wells 114a, and need not pass therebetween.) In FIG. 1, only some of the microchannels 112a and 112b are labeled (with reference numerals), for illustrative clarity. FIGS. 1A and 1B refer generally to a microchannels 112 which may be either of one of the first set of microchannels 112a or one of the second set of microchannels 112b. FIG. 1C shows only four (of the 120) microchannels 112a and 112b, and some are labeled with reference numerals.

The microchannels may have a width (or side length) of approximately 30 μm. The microchannels may all have the same width as one another. The microchannels may be square in cross-section, having a depth similar to their width, and straight sidewalls. The microchannels may have other, such as tapered or semi-circular cross-sections. Generally, the microchannels may be sized and shaped to accommodate (and selectively facilitate) the transport (in fluid) of single cells from the center well to the side wells. The microchannels may each have a volume of approximately 18 nL.

FIG. 1A shows the microchannels 112 as being level (assuming that the MA chip is in a Petri dish that is on a level tabletop, for example). The microchannels may be inclined towards the side wells 114 to aid in positive pressure-driving fluid flow from the center well to the side wells—in other words, a microchannel may be shallower at its center well end, and deeper at its side well end. The width of a microchannel may be uniform along its entire extent (length) from the center well to a side well, or it may be varied along its length. Generally, all of the microchannels on a given MA chip will have the same width and depth dimensions as one another, but it is possible that some microchannels may have different width and depth dimensions than others. (In FIG. 1, it is shown that some microchannels 112a are shorter than others 112b). MA chips may be made having microchannels of uniform width (and depth) as one another. Different MA chips may be produced to have different size (namely width and/or depth)—albeit, uniform with one another for a given MA chip—microchannels.

A cap 120 may be disposed over the center well 110. The cap may be in the form of a cylinder, having an outer diameter of approximately 5 mm and an inner diameter (or a hole therethrough) of approximately 3.0 mm, and a uniform bore from one end to the other end of the cylinder. The length of the cap may be approximately 5 mm. The cap may be formed of plastic, such as PDMS, is separate from, and is an element used in conjunction with the MA chip 100. The cap is shown spaced away from the MA chip in the figure. The cap may have a volume of approximately 112 μL. The hole (bore) extending through the cap may have a diameter of approximately 1.5 mm. The cap may be formed integrally with the MA chip, rather than as a separate piece.

As shown in FIG. 1A, a cap 120 may be disposed atop the center well 110 to connect a pipette tip (not shown) containing 120 μL cell suspension with the single center well for the easy loading of a large volume (e.g., 120 μL) cell suspension into a large number (e.g., 120) of side wells containing a small volume (e.g., 1 μL) with a single cell suspended therein for cloning or retrieval.

The cap 120 is open at its top and bottom surfaces. The bottom surface of the cap may be formed with a lip or shoulder extending from its bottom (as viewed) surface so that it extends slightly within the top of the center well to temporarily secure it in place during loading of the cell suspension. The cap is adapted in use to be disposed over the center well, and functions in the manner of a funnel (albeit cylindrical, rather than conical), facilitating loading of the cell suspension into the center well. The cap is, of course, not closed at its top surface, is analogous to a chimney, functions as a guide, and may be referred to as a "barrel", or a "flue", or a "duct".

In order to identify the many individual side wells, and readily distinguish them from one another, indicia may be provided on the top surface 102a of the MA chip. For example, a set of relatively small micrometer-scale (μm-scale) numbers ranging from "1" to "120" may be located on the top surface of the MA chip closely adjacent to (such as radially inward/inboard of) each of the individual side wells, to indicate (uniquely identify) corresponding side wells under microscopic observation. The μm-scale markings are omitted from FIG. 1. Some of these μm-scale markings may be visible in FIG. 1C. Additionally, a set (or subset) of relatively large millimeter-scale (mm-scale) numbers, such as even numbers ranging from "2" to "120" may be located on the top surface of the MA chip closely adjacent to (such as radially outward/outboard of) every other one of the side wells—in other words, radially outward of the second set of side wells 112b at the greater radius (r2) from the center of the MA chip—to indicate corresponding side wells under naked-eye observation. The mm-scale markings for odd-numbered side wells 112a may be omitted from the product, due to space consideration. (Alternatively, mm-scale odd numbers ranging from "1" to "119" may be disposed outboard of the first set of side wells 112a, and mm-scale markings for even numbered side wells may be omitted. Alternatively, mm-scale numbers for all of the side wells may be include, if space permits.) These mm-scale markings are visible in FIGS. 1A and 1C. The mm-scale numbers should correspond to the μm-scale numbers for the given side wells. Other indicia (e.g., markings, letters, colors, symbols) may be used to identify and distinguish individual ones (or groups) of the side wells. Some or all of the indicia may be disposed on the bottom surface of the MA chip to identify side wells. If the side wells do not extend completely through the MA chip, their bottoms could bear markings identifying the individual side wells.

Design and Fabrication of the MA Chip

The MA chip may be fabricated by conventional photolithography and polydimethylsiloxane (PDMS) molding techniques. PDMS belongs to a group of polymeric organosilicon compounds that are commonly referred to as silicones. PDMS is the most widely used silicon-based organic polymer, and is particularly known for its unusual theological (or flow) properties. PDMS is optically clear, and, in general, inert, non-toxic, and non-flammable. It is also called dimethicone and is one of several types of silicone oil (polymerized siloxane). Its applications range from contact lenses and medical devices to elastomers.

The MA chip design may be drawn using AutoCAD software (Autodesk) and then printed out as 4-inch glass photomasks (Photo Sciences, Inc.). The PDMS MA chip may be fabricated by standard photolithography and elastomeric molding. Briefly, SU-8 3025 negative photoresist (MicroChem Corp.) may be spin-coated onto a 4-inch silicon wafer (Silicon Quest International Inc.) at 2000-rpm (Laurell Technologies Corp.) for 1-min to form a sheet of 30-μm thick. After baking, exposing to UV light, and developing, mixed Polydimethylsiloxane (PDMS; 10A:1B; Dow Corning Corp.) may be poured onto the photoresist mold and heated at 80° C. for 25 min. After curing, the PDMS sheet of 1-mm thickness may be peeled off, and holes (for the wells) may be drilled by puncher (Ted Pella, Inc). The round PDMS MA chip is capable of automatically and closely sealing with a commercial Petri dish of 8.5 cm diameter (Fisher Scientific) without generation of air bubble. If desired, the MA chip can be sterilized by standard autoclave.

Besides PDMS, MA chips can also be fabricated by other materials including PMMA (poly(methyl methacrylate)), PS (polystyrene), and PC (Polycarbonate).

PMMA, also known as acrylic or acrylic glass as well as by the trade names Plexiglas, Acrylite, Lucite, and Perspex, is a transparent thermoplastic often used in sheet form as a lightweight or shatter-resistant alternative to glass.

PS is a synthetic aromatic polymer made from the monomer styrene. PS can be solid or foamed. General purpose PS is clear, hard, and rather brittle. It is an inexpensive resin per unit weight. It is a rather poor barrier to oxygen and water vapor and has a relatively low melting point. PS is one of the most widely used plastics.

PC is a group of thermoplastic polymers containing carbonate groups in their chemical structures. Polycarbonates used in engineering are strong, tough materials, and some grades are optically transparent. They are easily worked, molded, and thermoformed. Because of these properties, polycarbonates find many applications.

Isolating and Retrieving Single Cells

FIGS. 2A-2E illustrate an exemplary microfluidic aliquoting method 200 which may be performed to achieve the isolation and retrieval (or cloning) of single cells, using the MA chip 100 described hereinabove. The method, or operational process, is presented in a sequence of steps. Some of the steps or portions thereof may be performed in a different order than described herein. Estimated times to perform each of the steps may be mentioned.

Step 1 (202, ASSEMBLY):

The MA chip 100 may be placed into a Petri dish (not shown, see Appendices). The MA chip 100 may have a diameter of 6 cm, the Petri dish may have a diameter of 8.5 diameter. Due to the excellent properties of thin PDMS sheet in elasticity and flexibility, the MA chip can rapidly recover its flat shape even after having been rolled up, and then can closely conform to and seal with a rigid planar surface, such as the bottom of the Petri dish, without generation of air bubbles. This step is estimated to require 0.1 minutes (6 seconds) to complete.

Step 2 (204, CAPPING):

The cap 120 may be placed onto the top surface of the MA chip 100, atop the center well 110. (See FIG. 1A) The cap may be in the form of a cylinder. The center well may have a diameter of 3 mm. The cap may have an OD of 5 mm (sufficient to overlap/be bigger than the center well), and a hole extending through the cap may have a diameter of 1.5 mm. The cap may be aligned with its hole over the center well to allow for the introduction of a suspension of cells into the center well with a pipette. The cap may have a height of 5 mm. A PDMS cap disposed over the center well facilitates easily loading liquids (cell suspensions) into the MA chip by using pipette. This step is estimated to require 0.1 minutes (6 seconds) to complete.

The PDMS cap contains through hole of 1.5 mm in diameter and 5 mm in depth. Those dimensions are well compatible with 100-1000 μL pipette tip to load liquid into the MA chip without leakage.

Step 3 (206, ALIQUOTING):

A cell suspension (not shown), such as having a volume of 120 μL, may be injected for aliquoting into the center well (inlet) of the MA chip, via the cap, with a pipette having a 100-1000 µL pipette tip (not shown, see Appendices). This step is estimated to require 1 minute (60 seconds) to complete.

Due to uniform pressure distribution around the inlet, the cell suspension can be substantially simultaneously and uniformly distributed into the many (such as 120) side wells 114, resulting in random and reliable single-cell isolation. A positive pressure-driving flow may push (carry, move, transport) single cells from the center well (inlet) 110, via the microchannels 112 (112a, 112b) to the side wells (outlets) 114 (114a, 114b). This may be referred to as "microfluidic aliquoting".

After aliquoting, 100 µL cell-free media was dropped into the center well for pushing possible single cells within microchannels (1.8% in probability) into outlets (side wells). In other words, after loading 120 µL cell suspension into MA chip by pipette, one single cell may be occasionally residual into microchannels (1.8% in probability). By adding 100 µL cell-free media into the center well, a positive hydrostatic pressure will generate from center well to side wells. The positive hydrostatic pressure will push the residual single cells to flow into the side wells.

Step 4 (208, Identification):

Single cells in the side wells 114 may be identified under inverted microscope with a speed of 1 well/s and then noted according to the micrometer-scale numbers which are located inboard of the side wells and specially designed for microscopic observation. Because the field of inverted microscope by ×10 objective (2 mm in diameter) is larger than the size of MA chip well (1.5 mm in diameter), single side wells only containing single cells can be rapidly distinguished This step is estimated to require 1 second per well, or a total of 2 minutes (120 seconds) to complete (for 120 side wells).

Distribution of 123 isolated single cells into wells showed that, under the influence of microfluids, almost all single cells were located in the extension direction of the microchannel. In other words, under the effect of positive pressure from the center well to the side wells, all single cells may finally flow into the side wells. The exact location of each single cell in each 1.5 mm diameter side well may be different, from side well to side well. But the cells are likely to be located in the crossover field (intersection) of the microchannel and the side wells (namely, in the area in radially-innermost area of the side well which is just beyond the end of the microchannel connecting to the side well).

Step 5 (210, Retrieval):

According to the millimeter-scale even numbers which are located outboard of the side wells 114b and appropriately-sized for naked-eye observation, single cells of interest may conveniently and directly be retrieved by pipette (not shown) with a 0.1-2.5 µL pipette tip inserted into the side wells from the top surface of the MA chip.

Finally, cells were harvested from Petri dish, dispensed as a cell suspension, counted under microscope, loaded into MA chip, and retrieved as single-cell suspensions by using air-displacement-pipette (eppendorf).

Hereinabove is described a whole process for obtaining single cells by using the MA chip. The process to prepare a single-cell suspension with known cell numbers for loading into the MA chip may include the following 4 steps. 1) Drop 1 µL single cell suspension onto Petri dish by pipette. 2) Count cell numbers under inverted microscope. 3) Add 119 µL cell-free media into 1 µL single cell suspension. 4) Collect total single cells suspension with known cell numbers for microfluidic aliquoting. Then, the Steps 1-5 set forth above (Assembly, Capping, Aliquoting, Identification, Retrieval) above may be performed.

In lieu of a cap, a PDMS (or other material) mat may be disposed onto the MA chip (which may be referred to as a "MA dish"). The mat may have a thickness of 5 mm, and there may be a 1.5 mm diameter hole in the center of mat. The following steps may be performed in an exemplary procedure.

1) Put the 120-Well MA Dish onto the surface of a tissue culture dish.
2) Put the mat onto the MA dish. The 1.5 mm diameter hole should be aligned with the 3 mm central well in the vertical direction.
3) Aspirate more than 120-µL less than 1 cell/µL single cell suspension into a pipette tip.
4) Insert the pipette tip into the mat hole.
5) Load single cell suspensions into the 120 side wells by pushing down the pipette button.
6) Each side well may be filled with 1 µL cell suspension within 30 seconds.
7) Remove the pipette tip and mat.
8) Identify each side well, mark all side wells with single cell, and transfer single cells into vials by pipette for subsequent PCR experiment.
9) Alternatively, the single cells can be left within side wells to culture to form cell cloning.

Some Comments and Conclusions

The technology, functionality, and applicability of microfluidic aliquoting for the isolation of various single cells, independent of cell size, shape, and mobility has been described (and demonstrated). Microfluidic aliquoting allows for selective isolation of single cells from few cells, which is significantly important for precious clinical samples where cell numbers are limited, and from millions of cells, which can be potentially used to isolate CTCs (circulating tumor cells) from blood. It is also highly compatible with single-cell cloning, where viability of single cells are well maintained, and single-cell PCR, where 40 nanoliter single-cell suspensions can be prepared within 10 minutes. Moreover, MA chips are low-cost equaling to cost of 1.7 g PDMS (about $0.2) and easy realization of mass production without requiring bonding and valves, making them immediately available for single-cell researchers in common laboratories.

The feature of high-throughput aliquoting, 120 aliquots per operation, may result in a single (one) MA chip having an enrichment factor (EF) of 120. Therefore, in theory, one target cell can be successfully isolated from millions of cells via three or four MA chips, and a corresponding EF may be $1.7 \times 10^6$ and $2.1 \times 10^8$, respectively. Therefore, the MA chip has a high efficiency in cell recovery.

The MA chip can effectively isolate (singulate) single cells from few cells. Different MA chips having different size microchannels may be compatible with a variety of cell types, independent of cell size, shape, and mobility, such as single budding yeast of 4 µm diameter, single suspended T cell of 8 µm diameter, single MDA-MB-231 breast cancer cell of 16 µm diameter, and moving *Trypanosoma brucei* of 22 µm length and 3 µm width.

The size of channels including width and depth should be larger than the diameter of cells. This can decrease cell damage during transfer within microchannels—cells can easily be transported into the side wells from the center well. In this case, both width and depth of microchannel are 30 µm, which are larger than the tested cell diameters. Generally, microchannels with dimensions (width and depth) greater than the cell diameter are acceptable.

Even if there are only a few cells (such as 2-20 cells) in the original suspension, the MA chip has the ability to isolate single cells.

Due to negligible damage to cell viability, MA chips can also be used to selectively isolate single cells based on their adherent status even though there may be no obvious difference in morphology at the state of suspension. The desired cell could be retrieved by adding tiny trypsin into corresponding well or directly lysed under adherent status with negligible lysate loss due to positive pressure-driving flow, providing a potential way to study genotype-phenotype correlation at the single-cell level.

Due to rapid isolation and easy identification of single cells, high cell viability, and convenient transfer of submicroliter single-cell suspension, MA chips are well compatible with single-cell cloning, PCR, and sequencing. Wide type (WT) and PTEN knock out (KO) SUM 159 cells were used as proof-of-concept experiments. PTEN KO cells were generated by transient transfection with plasmids encoding sgRNA targeting PTEN (Phosphatase and tensin homolog) and Cas9 protein into SUM 159 cells. After single-cell isolation by MA chips, cells proliferated normally and cell counts at indicated time points were determined. Results showed that PTEN KO cells had shorter average doubling time of 25.9 h than that of WT cells of 28.3 h, which was consistent with previous studies that depletion of PTEN could promote cell proliferation.

The methods and apparatus disclosed herein may be used to identify and isolate single cells from a complicated matrix, e.g. single CTCs from blood, wherein the CTCs are captured in the side wells after single or multistep MA Chip operations. The methods and apparatus disclosed herein may be used to identify and isolate single cells and objects from a complicated matrix, e.g. to isolate single objects including bacterial, beads, particles, virus from a matrix, e.g. isolating Tuberculosis cells, and to isolate single clones, e.g. isolating yeast cell of a particular genotype/phenotype.

Distinguishing Over U.S. Pat. No. 6,632,656

The MA chip 100 of the present invention bears some similarities with the rotatable disc (18) of the aforementioned U.S. Pat. No. 6,632,656 ("Thomas"). They are both generally in the form of a disc. Thomas' channels have a width of 20-30 µm. The microchannels 112 may have a width of approximately 30 µm.

The MA chip 100 of the present invention may be distinguished from the rotatable disc (18) of the aforementioned U.S. Pat. No. 6,632,656 ("Thomas"), inter alia, as follows:

Thomas' chambers (2, 3, 7) appear to be located in a central portion of his disc. An outer portion of his disc is occupied by a waste channel (10). The side wells 114 (114a, 114b) of the MA chip disclosed herein are located at an outer portion of the MA chip.

Thomas' channels (6) comprise an inlet channel (1), followed by a chamber (2), followed by another channel (4), followed by a chamber (3), followed by an outlet channel (5) connected to a waste channel (10). The channels 112 (112a, 112b) of the MA chip disclosed herein extend from the center well (inlet) to the side wells (outlets), without anything (other chambers or wells) disposed therebetween.

Thomas uses rotation and centrifugal force to move cells in his channels, from chamber-to-chamber. The process 200 disclosed herein, using the MA chip disclosed herein, relies primarily on positive pressure to move cells from the center well (inlet) to the side wells (outlets).

Thomas' chambers, into which cells are moved by centrifugal force, are closed. The side wells described herein, into which cells are moved primarily by positive pressure, are open (and accessible from the top surface of the MA chip).

In Thomas' device, liquids and cells will flow out of the device through channels. However, in the MA chips described herein, all loaded liquids containing cells from the inlet (center well) are totally collected and stored into the outlets (side wells). There is no liquid flow out of the device. The way to collect sample (liquids plus cells) is totally different.

The MA chips described herein focus on aliquoting (dividing a sample into many equals with the same volume and no sample loss). In contrast, Thomas' device focuses on filtering, capturing cells into closed chambers and allowing liquid flow out of the device.

Thomas uses centrifugal force provided by specific centrifugal machine to load liquid into device. The present invention uses only a common air displacement pipette (all labs have) to easily load liquid such as cell suspension into MA chip. This will significantly reduce the reliance of device to external instrument such as centrifugal machine.

The size of the side wells disclosed herein is approximately 1.5 mm in diameter. This dimension is important for the easy identification of single cells within side wells under microscope and easy retrieval of liquid within side wells by 0.1-2.5 µL pipette tip. Because the field of inverted microscope by ×10 objective (2 mm in diameter) is larger than the size of MA chip well (1.5 mm in diameter), single wells only containing single cells can be rapidly distinguished (1 well/s). Thomas' chambers (2, 3, 7) are significantly larger than the side wells of the MA chip. Thomas describes circular 'wells' of about 400-600 µm diameter. Thomas also describes channels having a depth of 50 µm or 100 µm and a width of 100 µm, significantly larger (particularly in cross-sectional area, which is relevant to flow) than the microchannels described herein.

Thomas' device is mainly used for performing cell growth and analysis for example drug screening. The object is a great number of cells and the purpose is plenty of cells-based drug screening. The MA chip disclosed herein is primarily used to for single-cell sorting and isolation, and the object is individual cells and the purpose is single cells-based analysis including single-cell cloning, PCR, and sequencing.

The MA chip disclosed herein has excellent ability in target cell separation or sorting from cell populations such as sorting and isolating single CTCs (circulating tumor cells) from blood. In contrast, Thomas' device does not have this function, or capability to separate target cells (isolate individual cells).

Appendices

Appended hereto, and forming part of the disclosure hereof, are the following:

(A) Manuscript: an 8 page paper entitled Microfluidic aliquoting for single-cell isolation by Kai Zhang & Lidong Qin, Department of Nanomedicine, Houston Methodist Research Institute, Houston, Tex. 77030, USA (B) Figures: illustrations referred to in the Manuscript (A)

(C) Supplementary Information: descriptions of some of the illustrations in Figures (B).

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

What is claimed is:

1. A microfluidic aliquot (MA) chip for performing single-cell isolation, comprising:
a chip in the form of a disc having a radius, a center, a top surface, a bottom surface, an outer edge and a thickness;
a single center well (inlet) disposed substantially at the center of the chip, extending into and accessible from the top surface of the chip;
a plurality of side wells (outlets) disposed in an annular outer portion of the chip, extending into and accessible from the top surface of the chip;
a plurality of channels extending into the bottom surface of the chip and extending from the center well to the side wells in fluid communication with the center well and the side wells;
a first set of the plurality of side wells are disposed at a first radius (r1) from the center of the chip; and
a second set of the plurality of side wells are disposed at a second radius (r2) from the center of the chip;
wherein the second radius (r2) is greater than the first radius (r1);
the first and second sets of side wells are interleaved such that the second set of side wells are disposed at circumferential positions between the first set of sixty side wells.

2. The MA chip of claim 1, wherein:
the chip comprises a thin sheet of flexible or semi-rigid material selected from the group consisting of polydimethylsiloxane (PDMS), PMMA (poly(methyl methacrylate)), PS (polystyrene), and PC (polycarbonate).

3. The MA chip of claim 1, characterized by at least one of:
the chip has a thickness of approximately 1 mm;
the chip is sized and shaped to fit within a Petri dish; and
the chip has a radius of approximately 3 cm.

4. The MA chip of claim 1, wherein:
the center well extends completely through the chip; and
the side wells extend completely through the chip.

5. The MA chip of claim 1, characterized by at least one of:
the center well has a diameter of approximately 3 mm; and
the center well has a volume of approximately 4 µl.

6. The MA chip of claim 1, characterized by at least one of:
at least some of the side wells each have a diameter of approximately 1.5 mm; and
at least some of the side wells each has a volume of approximately 1 µl.

7. The MA chip of claim 1, wherein:
the first and second sets of side wells are distributed evenly around the annular outer portion of the chip.

8. The MA chip of claim 1, wherein:
the annular outer portion of the chip extends from at least 70% of the radius of the chip to an outer edge of the chip.

9. The MA chip of claim 1, characterized by at least one of:
the channels extend radially from the center well to the side wells;
the channels extend only partially into the chip;
the channels have a width of approximately 30 µm; and
the channels are sized and shaped to accommodate transport of single cells from the center well to the side wells.

10. The MA chip of claim 1, further comprising:
a cap having a hole extending therethrough, adapted in use to be disposed atop the center well, for facilitating loading of a cell suspension into the center well.

11. The MA chip of claim 10, wherein:
the cap is cylindrical and comprises a lip or shoulder extending from a bottom surface thereof to within the center well to temporarily secure the cap in place during loading of the cell suspension.

12. The MA chip of claim 10, wherein:
the cap is formed integrally with the chip.

13. A microfluidic aliquot (MA) chip for performing single-cell isolation, comprising:
a chip in the form of a disc having a radius, a center, a top surface, a bottom surface, an outer edge and a thickness;
a single center well (inlet) disposed substantially at the center of the chip, extending into and accessible from the top surface of the chip;
a plurality of side wells (outlets) disposed in an annular outer portion of the chip, extending into and accessible from the top surface of the chip;
a plurality of channels extending into the bottom surface of the chip and extending from the center well to the side wells in fluid communication with the center well and the side wells;
relatively small µm-scale markings disposed inboard of at least some of the side wells for uniquely identifying the side wells under microscopic observation; and
relatively large mm-scale markings disposed outboard of at least some of the side wells for uniquely identifying the side wells under naked-eye observation.

14. The MA chip of claim 13, wherein:
the chip comprises a thin sheet of flexible or semi-rigid material selected from the group consisting of polydimethylsiloxane (PDMS), PMMA (poly(methyl methacrylate)), PS (polystyrene), and PC (polycarbonate).

15. The MA chip of claim 13, characterized by at least one of:
the chip has a thickness of approximately 1 mm;
the chip is sized and shaped to fit within a Petri dish; and
the chip has a radius of approximately 3 cm.

16. The MA chip of claim 13, wherein:
the center well extends completely through the chip; and
the side wells extend completely through the chip.

17. The MA chip of claim 13, characterized by at least one of:
the center well has a diameter of approximately 3 mm; and
the center well has a volume of approximately 4 µl.

18. The MA chip of claim 13, characterized by at least one of:
at least some of the side wells each have a diameter of approximately 1.5 mm; and
at least some of the side wells each has a volume of approximately 1 µl.

19. The MA chip of claim 13, wherein:
a first set of the plurality of side wells are disposed at a first radius (r1) from the center of the chip; and
a second set of the plurality of side wells are disposed at a second radius (r2) from the center of the chip;
wherein the second radius (r2) is greater than the first radius (r1).

20. The MA chip of claim 19, wherein:
the first and second sets of side wells are interleaved such that the second set of side wells are disposed at circumferential positions between the first set of sixty side wells.

21. The MA chip of claim 19, wherein:
the first and second sets of side wells are distributed evenly around the annular outer portion of the chip.

22. The MA chip of claim 13, wherein:
the annular outer portion of the chip extends from at least 70% of the radius of the chip to an outer edge of the chip.

23. The MA chip of claim 13, characterized by at least one of:
the channels extend radially from the center well to the side wells;
the channels extend only partially into the chip;
the channels have a width of approximately 30 μm; and
the channels are sized and shaped to accommodate transport of single cells from the center well to the side wells.

24. The MA chip of claim 13, further comprising:
a cap having a hole extending therethrough, adapted in use to be disposed atop the center well, for facilitating loading of a cell suspension into the center well.

25. The MA chip of claim 3, wherein:
the cap is cylindrical and comprises a lip or shoulder extending from a bottom surface thereof to within the center well to temporarily secure the cap in place during loading of the cell suspension.

26. The MA chip of claim 24, wherein:
the cap is formed integrally with the chip.

* * * * *